United States Patent
Takeuchi et al.

(10) Patent No.: US 6,245,880 B1
(45) Date of Patent: Jun. 12, 2001

(54) ORGANOPHOSPHOROUS COMPOSITION, METHOD OF PRODUCING ORGANOPHOSPHOROUS COMPOUND, POLYESTER COMPOSITION AND METHOD OF PRODUCING THE SAME

(75) Inventors: Hideo Takeuchi, Osaka; Maki Sato; Shoichi Gyobu, both of Ohtsu, all of (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 0 days.

(21) Appl. No.: 09/679,466

(22) Filed: Oct. 4, 2000

(30) Foreign Application Priority Data

| Oct. 8, 1999 | (JP) | 11-288022 |
| Dec. 15, 1999 | (JP) | 11-356031 |
| Dec. 15, 1999 | (JP) | 11-356062 |
| Feb. 23, 2000 | (JP) | 2000-045469 |

(51) Int. Cl.$^7$ ............... C08G 63/68; C07F 9/02
(52) U.S. Cl. ............ 528/287; 558/82; 558/122; 528/281; 528/285; 528/302; 528/308; 528/403; 528/414
(58) Field of Search ............ 558/82, 122; 528/281, 528/285, 287, 308, 302, 403, 414

(56) References Cited

U.S. PATENT DOCUMENTS

| 4,157,436 | 6/1979 | Endo et al. ............ 528/167 |
| 5,481,017 | 1/1996 | Kleiner . |
| 5,650,530 | 7/1997 | Buysch et al. . |
| 5,821,376 | 10/1998 | Rathfelder et al. . |

FOREIGN PATENT DOCUMENTS

| 49-45397 | 12/1974 | (JP) . |
| 50-17979 | 6/1975 | (JP) . |
| 10001490 | 1/1998 | (JP) . |

*Primary Examiner*—Samuel A. Acquah
(74) *Attorney, Agent, or Firm*—Kenyon & Kenyon

(57) ABSTRACT

A polyester having a good color tone can be obtained by using, as an ester-forming component, a compound derived from an organophosphorous composition comprising an organophosphorous compound represented by the general formula (1):

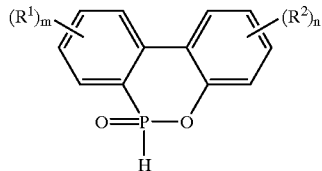

(1)

wherein $R^1$ and $R^2$ represent an organic group or a halogen atom, and m and n represent an integer of 0 to 4, provided that $R^1$ and $R^2$ may be the same or different when m or n is an integer of 2 to 4, and a divalent metallic compound in an amount more than 30 ppm and not more than 2300 ppm in terms of a divalent metal based on the organophosphorous compound.

20 Claims, No Drawings

ORGANOPHOSPHOROUS COMPOSITION, METHOD OF PRODUCING ORGANOPHOSPHOROUS COMPOUND, POLYESTER COMPOSITION AND METHOD OF PRODUCING THE SAME

BACKGROUND OF THE INVENTION

1. Field of the Invention

The present invention relates to an organophosphorous composition comprising, as a principal component, an organophosphorous compound represented by the general formula (1):

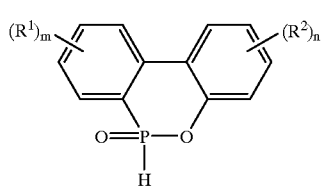

(1)

wherein $R^1$ and $R^2$ represent an organic group or a halogen atom, and m and n represent an integer of 0 to 4, provided that $R^1$ and $R^2$ may be the same or different when m or n is an integer of 2 to 4, and a predetermined amount of a divalent metallic compound.

The present invention also relates to a method of producing the organophosphorous composition represented by the general formula (1).

The present invention relates to an organophosphorous composition comprising an organophosphorous compound represented by the general formula (4):

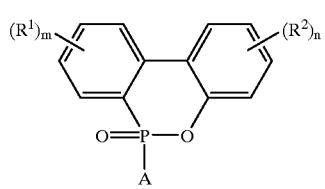

(4)

wherein $R^1$, $R^2$, m and n are as defined above and A represents an organic group which is the same as or different from that of $R^1$ and $R^2$, which is derived from the organophosphorous compound represented by the general formula (1) in the organophosphorous composition, and a predetermined amount of a divalent metallic compound.

The present invention also relates to a polyester composition comprising polyester having a predetermined amount of a phosphorous atom related to an organophosphorous compound wherein an organic group (A) in the general formula (4) is an ester-forming functional group (B), and a predetermined amount of a divalent metallic compound, and a method of producing the same.

The organophosphorous composition comprising the organophosphorous compound represented by the general formula (1) or (4) is used for various purposes, for example, raw materials for polymer compounds, lubricating oils, antioxidants for organic compounds, flame retarders, plasticizers, bactericides, color protection agents, polymerization initiators and the like. Particularly, those wherein an organic group (A) in the general formula (4) is an ester-forming functional group (B) are useful as a copolymer component of the polyester, and are capable of producing a flame-retardant polyester.

2. Description of the Related Art

Organophosphorous compounds (also referred to as "DOP", hereinafter) such as 6-oxo-(6H)-dibenzo-(c,e)(1,2)-oxaphosphorine, which are presented by the general formula (1), have hitherto been disclosed in production methods described in Japanese Examined Patent Publication (Kokoku) No. Sho 49-45397 and Japanese Examined Patent Publication (Kokoku) No. Sho 50-17979, and recent publications such as Japanese Unexamined Patent Publication (Kokai) No. Hei 10-1490, Japanese Unexamined Patent Publication (Kokai) No. Hei 7-145185, Japanese Unexamined Patent Publication (Kokai) No. Hei 8-99983 and Published Japanese Translation No. Hei 10-510545 of the PCT Application.

DOP has been produced by reacting an orthophenylphenol compound (also referred to as "OPP", hereinafter) represented by the general formula (2):

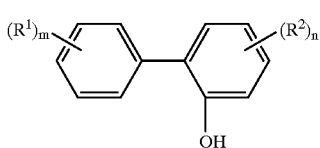

(2)

wherein $R^1$, $R^2$, m and n are as defined above, with a phosphorous compound such as phosphorous trihalide ($PX_3$: X represents a halogen atom), condensing the reaction product with heating in the presence of a Friedel-Crafts catalyst containing zinc chloride to produce a compound represented by the general formula (3):

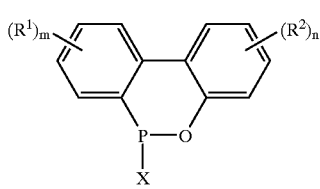

(3)

wherein $R^1$, $R^2$, m and n are as defined above and X represents a halogen atom, and hydrolyzing the compound (also referred to as "DOP-X", hereinafter) with water under heating.

In such a method, however, a zinc compound such as zinc chloride as the Friedel-Crafts catalyst used in the production of DOP-X is remained in the resulting DOP. Since the divalent metallic compound such as zinc compound forms a complex with DOP thus forming an insoluble matter during the reaction between DOP and the other organic compound, DOP containing a small amount of the divalent metal is required.

In case a compound derived from DOP, as a flame retarder component, is used in a copolymer component of the polyester, an antimony compound such as antimony trioxide used as a polymerization catalyst of the polyester is reduced by DOP, thereby causing a problem that the resulting polyester is blackish.

SUMMARY OF THE INVENTION

An object of the present invention is to provide a composition containing DOP, which does not form a complex during the reaction between DOP and an organic compound and can satisfactorily maintain a color tone of the resulting polyester even in case of using a compound derived from DOP in a copolymer component of a polyester.

Another object of the present invention is to provide a method which can produce DOP whose zinc content is reduced to the degree where a complex is not formed during the reaction with an organic compound, and to provide a method which can produce DOP capable of satisfactorily maintaining a color tone of the resulting polyester even in case of using a DOP-derived compound in a copolymer component of a polyester.

A still another object of the present invention is to provide the DOP derivative composition described above, and to provide a polyester having a good color tone and a method of producing the same using the DOP derivative composition.

The present inventors have studied intensively to solve the problems described above and found that the objects described above can be attained by the following means, thus completing the present invention.

The objects described above of the present invention can be attained by the following means.

1. An organophosphorous composition comprising, as a principal component, an organophosphorous compound represented by the general formula (1):

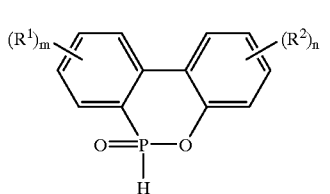

(1)

wherein $R^1$ and $R^2$ represent an organic group or a halogen atom, and m and n represent an integer of 0 to 4, provided that $R^1$ and $R^2$ may be the same or different when m or n is an integer of 2 to 4, the composition further comprising, as a compound other than the organophosphorous compound, a divalent metallic compound in an amount more than 30 ppm and not more than 2300 ppm in terms of a divalent metal based on the organophosphorous compound.

2. The organophosphorous composition according to claim 1, wherein the divalent metal is zinc.

3. The organophosphorous composition according to claim 1, wherein the compound other than the organophosphorous compound is a halogen compound, the content of the halogen compound is not more than 250 ppm in terms of an amount of a halogen atom based on the organophosphorous compound.

4. The organophosphorous composition according to claim 1, which does not substantially contain an organic compound other than the organophosphorous compound.

5. The organophosphorous composition according to claim 1, which is in the form of powder.

6. A method of producing an organophosphorous compound represented by the general formula (1):

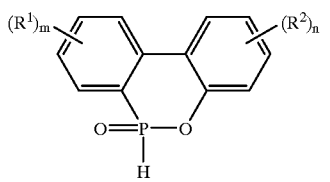

(1)

wherein $R^1$ and $R^2$ represent an organic group or a halogen atom, and m and n represent an integer of 0 to 4, provided that $R^1$ and $R^2$ may be the same or different when m or n is an integer of 2 to 4, which comprises the steps of:

reacting an orthophenylphenol compound represented by the general formula (2):

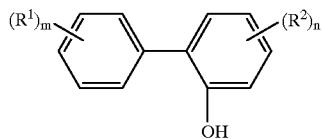

(2)

wherein $R^1$ and $R^2$ are as defined above, with phosphorous trihalide ($PX_3$: X represents a halogen atom) and condensing the reaction product with heating in the presence of a Friedel-Crafts catalyst containing zinc chloride to produce an organophosphorous compound represented by the general formula (3):

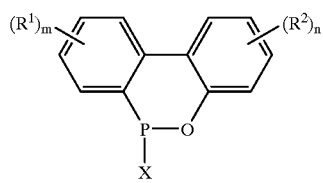

(3)

wherein $R^1$ and $R^2$ are as defined above and X represents a halogen atom; and hydrolyzing the compound represented by the general formula (3) with water; the compound represented by the general formula (3) and water in the hydrolysis step are used in an equimolar ratio and that the method further comprises a step of purifying the organophosphorous compound represented by the general formula (1) by further hydrolyzing the organophosphorous compound represented by the general formula (1), which is obtained by passing through the hydrolysis step, followed by cyclodehydration.

7. The method of producing the organophosphorous compound according to claim 6, wherein the compound represented by the general formula (2), which has purity of not less than 80% and less than 100%, is subjected to the reaction after remarkably purifying by washing with an organic solvent.

8. The method of producing the organophosphorous compound according to claim 6, wherein the compound represented by the general formula (3) is subjected to a hydrolysis step after subjected to a purification step.

9. The method of producing the organophosphorous compound according to claim 6, wherein the content of a zinc compound is adjusted more than 30 ppm and not more than 2300 ppm in terms of metallic zinc based on the organophosphorous compound represented by the general formula (1).

10. The method of producing the organophosphorous compound according to claim 6, wherein the content of a halogen compound is not more than 250 ppm in terms of an amount of a halogen atom based on the organophosphorous compound represented by the general formula (1).

11. The method of producing the organophosphorous compound according to claim 6, wherein an organic compound other than the organophosphorous compound represented by the general formula (1) is not substantially contained.

12. The method of producing the organophosphorous compound according to claim 6, wherein the organophosphorous compound represented by the general formula (1) is in the form of powder.

13. An organophosphorous composition produced by derivation of an organophosphorous compound in the organophosphorous composition of claim 1 into an organophosphorous compound represented by the general formula (4):

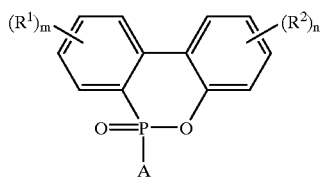

(4)

wherein $R^1$ and $R^2$ represent an organic group or a halogen atom, m and n represent an integer of 0 to 4, provided that $R^1$ and $R^2$ may be the same or different when m or n is an integer of 2 to 4, and A represents an organic group which is the same as or different from that of $R^1$ and $R^2$.

14. The organophosphorous composition according to claim 13, wherein the organic group (A) in the general formula (4) is an organic group containing an ester-forming functional group (B).

15. A polyester composition comprising, as a principal component, a polyester obtained from an ester-forming component containing a dicarboxylic acid component and a diol component, the polyester containing, as the ester-forming component, an organophosphorous compound represented by the general formula (5):

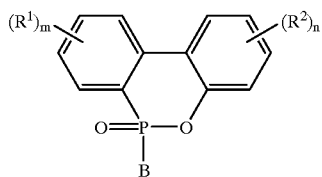

(5)

wherein $R^1$ and $R^2$ represent an organic group or a halogen atom, m and n represent an integer of 0 to 4, provided that $R^1$ and $R^2$ may be the same or different when m or n is an integer of 2 to 4, and B represents an ester-forming functional group, the polyester composition containing a divalent metallic compound in an amount not less than 1 ppm and not more than 150 ppm in terms of a divalent metal based on the polyester.

16. The polyester composition according to claim 15, which contains a divalent metallic compound in an amount not less than 1 ppm and not more than 50 ppm in terms of a divalent metal based on the polyester.

17. The polyester composition according to claim 15, wherein the divalent metal is zinc.

18. The polyester composition according to claim 15, which contains an organophosphorous compound represented by the general formula (5) as the ester-forming component of the polyester in an amount not less than 500 ppm and not more than 5000 ppm in terms of an amount of a phosphorous atom.

19. A method of producing the polyester composition of claim 15, which comprises reacting an ester-forming component containing a dicarboxylic acid component and a diol component, wherein the organophosphorous composition of claim 14 is used as the dicarboxylic acid component and/or the diol component.

20. The method of producing the polyester composition of claim 19, wherein an antimony compound is used as a condensation catalyst of the polyester.

As a result of obtaining such a new knowledge that the reduction of an antimony compound is suppressed in case a divalent metal compound is present in a DOP derivative compound used in a copolymer component of a polyester. The divalent metal compound is incorporated in the amount to the degree where a complex is not formed in DOP based on the knowledge according to the present invention.

Controlling the amount of the divalent metal compound based on DOP can attained the objects described above. By incorporating the divalent metal in the amount, which exceeds 30 ppm, based on DOP, the color tone of the polyester using the DOP-derived compound is maintained satisfactorily. From such a point of view, the amount of the divalent metal based on DOP is preferably controlled to 50 ppm or more. It is presumed the suppression of the reduction of the antimony compound is the result of the prior reduction of the divalent metal compound to the antimony compound. On the other hand, when the amount of the divalent metal based on DOP increases, a complex is liable to be formed during the reaction with an organic compound, thereby forming an insoluble matter. In case the polyester is spun, the operation properties tend to be lowered due to an increase in back pressure. Therefore, the amount of the divalent metal is preferably controlled to 500 ppm or less, more preferably 300 ppm or less, and most preferably 200 ppm or less, based on DOP.

A control of the content of the divalent metal within the predetermined range is easier than purification by complete removal of a catalyst residue after the synthesis of DOP, and is useful to simplify the purification step after the synthesis of DOP.

As the divalent metal, for example, various metals are used. To attain the objects described above, zinc is preferably used as a catalyst for producing DOP and is also preferable in view of the preparation of the above organophosphorous composition.

Usually, a halogen compound produced during the production is remained in the organophosphorous composition containing DOP as a principal component; the content of the halogen compound is preferably controlled to 250 ppm or less in terms of an amount of a halogen atom based on DOP. The smaller the amount of the halogen atom based on DOP, the better. The amount of the halogen atom is preferably controlled to 150 ppm or less. By reducing the amount of the halogen content, the formation of the reaction impurity (for example, dimerization of a diol component such as ethylene glycol into diethylene glycol) during the production of a polyester using a DOP-derived compound, thereby making it possible to prevent a decrease in melting point of the polyester and to improve the heat resistance.

Those, which are obtained by substantially removing an organic compound other than DOP, e.g. OPP as a raw material of DOP, from the organophosphorous composition containing DOP as the principal component, are superior in whiteness, and do not require a melt-purification step such as vacuum distillation, thus making it possible to simplify the purification step. Such an organophosphorous composition is usually in the form of powder, and the powdered substance is easy to handle and is superior in solubility in an organic solvent and productivity. The sentence "does not substantially contain an organic compound other than DOP" refers to the case where the purity of DOP in the organophosphorous composition is high to the degree where the organophosphorous composition is in the form of powder, for example, the case where the content of the organic compound other than DOP in the organophosphorous composition is 10000 ppm or less.

In the method of producing DOP of the present invention, by using DOP-X and water in an equimolar ratio in the hydrolysis step, the formation of a waste liquor containing a hydrogen halide gas (e.g. hydrochloric acid waste liquor, etc.) is suppressed and, moreover, the hydrogen halide gas can be quantitatively separated and the content of a halogen compound in DOP can be reduced. By providing, as a purification step (b) for improving the purity of the resulting DOP, a step of cyclodehydration after furthers hydrolyzing DOP, the catalyst residue, halogen compound and impurity contained in OPP can be efficiently removed.

In the production of DOP-X, by subjecting to a step (c) of remarkably purifying by washing crude OPP as a raw material in an organic solvent, the content of an organic compound other than the desired compound in DOP-X and DOP can be reduced and the purity of DOP-X and DOP can be improved by a simple operation.

By subjecting to the step of hydrolyzing to DOP-X after subjected to the purification step (a), not only the removal of the catalyst residue, halogen compound and impurity contained in OPP, but also the control of the content of a zinc compound in DOP can be effectively conducted.

According to such a production method of the present invention, the content of the catalyst residue, halogen compound, and organic compound other than the desired compound contained in OPP can be reduced. It is preferable to control the content of the zinc compound and that of the halogen compound based on DOP so that they are the same as those in the DOP composition. Preferred are powdered products wherein the organic compound other than DOP, such as OPP as a raw material, was substantially removed.

The organophosphorous composition comprising the organophosphorous compound represented by the general formula (4) derived from the organophosphorous compound in the organophosphorous composition containing DOP as a principal component, and a predetermined amount of the divalent metal compound, is a DOP derivative incorporated with an organic group (A) appropriately according to various purposes of DOP, and also contains a predetermined amount of the divalent metal compound similar to the organophosphorous composition containing DOP as the principal component. Typical examples of the organic group (A) include an organic group containing an ester-forming functional group (B), and the DOP derivative having an organic group represented by the general formula (5) is used as the copolymer component of the polyester, thereby imparting the flame retardancy to the polyester.

The polyester composition, which contains the organophosphorous compound represented by the general formula (5) as the ester-forming component and the divalent metal compound in an amount not less than 1 ppm and not more than 150 ppm in terms of an amount of a divalent metal, exhibits good heat resistance and flame retardancy. Those, which contain the divalent metal compound in an amount not less than 1 ppm and not more than 150 ppm in terms of an amount of a divalent metal based on the polyester, have an improved color tone of the polyester and exhibits good stability.

In case the amount of the divalent metal is less than 1 ppm based on the polyester, when using an antimony compound as a polymerization catalyst of the polyester, the reduction of the antimony compound can be not sufficiently suppressed and the color tone of the polyester is not sufficiently improved. On the other hand, when the amount of the divalent metal exceeds 150 ppm, the thermal stability of the polyester is lowered and, moreover, the divalent metal forms a complex with a dye during the dyeing of the polyester, thereby causing a discoloration referred to as chameleon discoloration, which is not preferable. Therefore, the amount of the divalent metal is preferably controlled to 50 ppm or less, and more preferably 30 ppm or less.

As the divalent meal, zinc is preferable because it is superior in improvement in color tone of the polyester.

It is preferable in view of the heat resistance and flame retardancy that the polyester composition contains the organophosphorous compound represented by the general formula (5) as the ester-forming component of the polyester in an amount not less than 500 ppm and not more than 500000 ppm in terms of a content of a phosphorous atom. The larger the content of the phosphorous atom, the better the flame retardancy. Therefore, the content of the phosphorous atom is preferably controlled to 2000 ppm or more, and more preferably 3000 ppm or more. On the other hand, when the content of the phosphorous atom increases, lowering of the physical properties of the polyester and lowering of the operation properties in the production of the polyester tend to occur, the content of the phosphorous atom is preferably controlled to 15000 ppm or less, and more preferably 6500 ppm or less.

The polyester composition of the present invention can be produced by various methods, it is preferable to use, as a dicarboxylic acid component and/or a diol component, a compound represented by the general formula (5) (wherein the organic group (A) of the compound (DOP derivative compound) represented by the general formula (4) is an ester-forming functional group (B)) containing a predetermined amount of the divalent metal in the method of producing a polyester from an ester-forming component containing the dicarboxylic acid component and diol component. When using an antimony compound as the polymerization catalyst of the polyester, the reduction of the antimony compound is suppressed by a predetermined amount of the divalent metal compound in the organophosphorous composition, which is preferable.

DETAILED DESCRIPTION OF THE PREFERRED EMBODIMENTS

The method of preparing the organophosphorous composition comprising an organophosphorous compound (DOP) represented by the general formula (1):

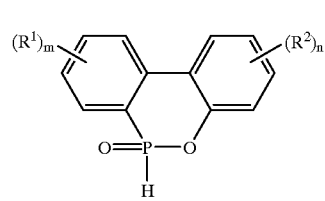

(1)

wherein $R^1$ and $R^2$ represent an organic group or a halogen atom, and m and n represent an integer of 0 to 4, provided that $R^1$ and $R^2$ may be the same or different when m or n is an integer of 2 to 4, and a predetermined amount of a divalent metallic compound according to the present invention is not specifically limited as far as the divalent metal compound is contained in the organophosphorous composition in the predetermined amount based on DOP. The organophosphorous composition may be those containing a predetermined amount of the divalent metal compound as impurity of DOP as a result of the production of DOP, or may be prepared by separately incorporating the divalent metal compound into DOP so that the amount of the divalent metal compound is a predetermined amount.

Examples of the divalent metal compound include zinc compound, manganese compound, magnesium compound, calcium compound, barium compound, copper compound, iron compound, cobalt compound and the like.

Examples of the organic group as for $R^1$ and $R^2$ in the general formula (1) include hydrocarbon group (e.g., straight-chain or branched alkyl group having about 1 to 4 carbon atoms; aryl group such as phenyl group; aralkyl group such as benzyl group; cycloalkyl group); alkoxy group,aryl group and aralkyl group corresponding to the hydrocarbon group ; and carboxyl group or ester group thereof. Examples of the halogen atom include chlorine atom, bromine atom and the like.

DOP is prepared in the following manner, for example, an orthophenylphenol compound (OPP) represented by the general formula (2):

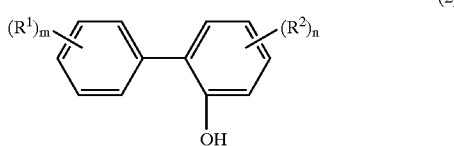

(2)

wherein $R^1$, $R^2$, n and m are as defined above, is reacted with phosphorous trihalide ($PX_3$: X represents a halogen atom such as chlorine atom, bromine atom or the like) and the reaction product is condensed with heating in the presence of a Friedel-Crafts catalyst to produce a compound (DOP-X) represented by the general formula (5):

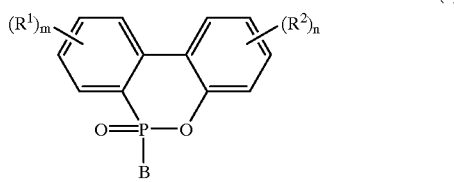

(5)

wherein $R^1$, $R^2$, n and m are as defined above and X represents a halogen atom.

A molar ratio of OPP to phosphorous trihalide (OPP:phosphorous trihalide) is usually from about 1:1 to 1:2, and preferably from about 1:1.1 to 1:1.5.

Examples of the phosphorous trihalide include phosphorous trichloride, phosphorous tribromide and the like. Usually, phosphorous trichloride is used as the phosphorous trihalide. Since almost of the halogen compound remained in the organophosphorous composition of the present invention is derived from the phosphorous trihalide, the content of the halogen compound when using phosphorous trichloride as the phosphorous trihalide is the same as that of a chlorine compound.

As the Friedel-Crafts catalyst, zinc chloride is preferably used. There can be employed, for example, metal halide (e.g. cuprous chloride, cupric chloride, tin chloride, mercury chloride, iron chloride, etc.), metallic zinc, metallic aluminum, metallic copper, or oxide of these metals, which can be converted into a halide in the reaction system, in addition to zinc chloride.

The catalyst is used so that the organophosphorous composition of the present invention contains at least a predetermined amount of the divalent metal compound, usually is used in an amount within the range from about 0.05 to 3 parts by weight, and preferably from about 0.1 to 1 parts by weight, based on 100 parts by weight of OPP.

The reaction temperature is usually within the range from about 30 to 250° C., and preferably from about 50 to 230° C. The reaction time varies depending on the reaction conditions such as reaction temperature, amount of the catalyst and the like, usually is within the range from about 3 to 35 hours, and preferably from about 5 to 15 hours. The completion of the reaction is judged by a point of time where the evolution of a hydrogen halide gas caused with the progress of the reaction is terminated.

Then, hydrolyzing DOP-X with water under heating produce DOP. The reaction temperature of the hydrolysis is within the range from about 50 to 250° C., while the reaction time is within the range from about 1 to 10 hours.

The amount of water is not specifically limited as far as it is an equimolar amount or more relative to the amount of DOP-X. In case DOP-X and water react in an equimolar ratio,a waste liquor containing a hydrogen halide gas (e.g. hydrochloric acid waste liquor, etc.) is not produced and the hydrogen halide gas can be quantitatively separated, which is preferable. According to the method of reacting DOP-X and water in an equimolar ratio, DOP-X and water react in a molar ratio of 1:1 and the reaction is conducted while removing the hydrogen halide gas produced during the reaction according to the production rate of the hydrogen halide gas. The completion of the reaction is judged by a point of time where the evolution of a hydrogen halide gas caused with the progress of the reaction is terminated.

When using excess amount of water in the hydrolysis, DOP is further hydrolyzed and, therefore, the hydrolyzate of DOP is converted into DOP by cyclodehydration with heating after isolating the hydrolyzate of DOP. The cyclodehydration with heating is usually conducted at about 110–180° C. under reduced pressure within the range from about 10 to 15 kPa.

The hydrolysis can also be conducted in the presence of an organic solvent. Examples of the organic solvent include aromatic solvents such as toluene, o-xylene, m-xylene, p-xylene, ethylbenzene, chlorobenzene, dichlorobenzene and the like. The amount of the organic solvent is 1000 parts by weight or less, and preferably 500 parts by weight or less, based in 100 parts by weight of OPP as the raw material.

DOP is usually produced in such way. The organophosphorous composition of the present invention is prepared so that a predetermined amount of the divalent metal compound is contained in the resulting DOP in the production process of DOP and that the content of the halogen compound and that of the organic compound other than DOP are reduced.

The organophosphorous composition may take any form of bulk, flock, flake and powder, preferably is in the form of powder. The organophosphorous composition can be formed into powders by using various means such as pulverization. The powdered organophosphorous composition can be obtained by removing impurities in the organophosphorous composition using the following method.

In the method of producing DOP, the organophosphorous composition of the present invention can be prepared by a method (a) of purifying DOP-X after its production and a method (b) of purifying DOP-X after its hydrolysis.

In the method (a) of purifying DOP-X after its production, the catalyst residue and halogen compound can be removed and the content of the divalent metal compound in the resulting purifying DOP-X after its production can be controlled. Impurities contained in OPP can also be removed.

Specific examples of the method (a) include a method (a1) of washing with an organic solvent, a method (a2) of vacuum distillation and a method (a3) of recrystallization. Examples of the organic solvent in the method (a1) include aromatic solvents such as toluene, o-xylene, m-xylene, p-xylene, ethylbenzene, chlorobenzene, dichlorobenzene and the like. Among these organic solvents, toluene is preferable because it sufficiently dissolves impurities in OPP. The amount of the organic solvent is 0.05% by weight or more based on DOP-X and DOP-X can be washed with a small amount of the organic solvent. The upper limit of the amount of the organic solvent is not defined, preferably is 50% by weight or less based on DOP-X. The washing/purification of DOP-X is conducted by adding a predetermined amount of the organic solvent, dissolving DOP-X with stirring and removing the supernatant. The method (a2) of vacuum distillation is conducted at about 220–250° C. under reduced pressure of about 133 Pa. The method (a3) of recrystallization is conducted by recrystallizing from alcohol. Among these purification methods (a), the method (a1) is preferable because of its simple operation.

In the method (b) of purifying DOP after its hydrolysis, the purity of DOP is enhanced by removing the catalyst residue, halogen compound and impurities contained in OPP. DOP thus obtained is superior in whiteness because of high purity, and is in the form of fine powder.

In the purification method (b), when using an excess amount of water in the hydrolysis of DOP-X, the hydrolyzate of DOP is isolated and then the hydrolyzate of DOP is subjected to the purification (b1) in order to conduct cyclodehydration with heating. The hydrolyzate of the purified DOP is converted into a white crystal.

The purification (b1) of the hydrolyzate of DOP is appropriately conducted in the presence or absence of the organic solvent on hydrolysis. In case (b1-1) the organic solvent is absent on hydrolysis, the hydrolyzate of DOP is purified by the method of distilling the hydrolyzate of DOP, the method of recrystallization, or the method of adding an alkaline metal hydroxide, followed by heating, decoloring and deposition with acid. In the method of distillation and method of recrystallization, the same method as that of the purification methods (a) can be employed. Examples of the alkaline metal hydroxide include sodium hydroxide, potassium hydroxide, calcium hydroxide, magnesium hydroxide, aluminum hydroxide and the like. In the decoloring treatment, activated carbon, activated china clay or the like is used. In the deposition with acid, sulfuric acid, hydrochloric acid or the like is used.

In case (b1-2) the organic solvent is present on hydrolysis, the purification is conducted by separating the aqueous layer, optionally washing the oil layer with water several times while heating under pressure, removing residual water from the oil layer and subjecting to a decoloring treatment. If necessary, the hydrolyzate of DOP is purified by washing with water, washing with the organic solvent and filtration. In the decoloring treatment, the same method as described above can be employed.

In case the hdyrolysis reaction is conducted by using water in an equimolar amount relative to the amount of DOP-X, DOP is obtained as the reaction product. Therefore, the resulting DOP is subjected to the purification (b2) after the completion of the reaction. The purification (b2) of DOP can be conducted by the method of adding the organic solvent to DOP, followed by cooling, filtration of the product and washing with the organic solvent, the method of distillation or the method of recrystallization (b2-1). DOP obtained by the hydrolysis reaction using water in an equimolar amount relative to the amount of DOP-X can be subjected to the purification (b2-1) of DOP. Alternatively, the resulting DOP can also be subjected to the same purification (b2-2) by adding hot water and hydrolyzing DOP thereby converting into a hydrolyzate (b1: any of b1-1 and b1-2). In this case, the hydrolyzate of DOP is subjected to cyclodehydration after the purification (b2-2). The purification (b2) of DOP can also be conducted after the purification (b1) of DOP.

Among these purification methods (b), the method of further hydrolyzing the resulting DOP and purifying the hydrolyzate of DOP, followed by cyclodehydration is preferable (b2-2). The same operation as that of (b1-1) is preferable as the purification means in (b2-2). When the hydrolysis reaction is conducted by using water in an equimolar amount relative to the amount of DOP-X, a hydrochloric acid waste liquor is not produced and DOP can be efficiently purified by the hydrolysis, thereby making it possible to enhance the purity of DOP.

The content of the organic compound other than DOP can be reduced by the method (c) of using high-purity OPP as the raw material, in addition to the method described above. The high-purity OPP is usually prepared by washing OPP having a purity of 80% or higher with an organic solvent. Examples of the organic solvent include aromatic solvents such as toluene, o-xylene, m-xylene, p-xylene, ethylbenzene, chlorobenzene, dichlorobenzene and the like. Among these organic solvents, toluene is preferable because it sufficiently dissolves impurities in OPP. The amount of the organic solvent is 0.05% by weight or more based on OPP and OPP can be washed with a small amount of the organic solvent. The upper limit of the amount of the organic solvent is not defined, preferably is 50% by weight or less based on OPP. The washing/purification of OPP is conducted by adding a predetermined amount of the organic solvent, dissolving OPP with stirring and removing the supernatant.

The method of synthesizing OPP is described in Japanese Unexamined Patent Publication (Kokai) No. Sho 50-18444, Japanese Unexamined Patent Publication (Kokai) No. Sho 55-33417, Japanese Unexamined Patent Publication (Kokai) No. Sho 56-20533, Japanese Unexamined Patent Publication (Kokai) No. Sho 62-4442 and Japanese Unexamined Patent Publication (Kokai) No. Hei 5-201904. According to these methods, however, dibenzofuran, o-cyclohexenylcyclohexane, 2-cyclohexylphenol or the like as a starting material of OPP is remained as impurity in the resulting OPP.

The organophosphorous composition comprising DOP as a main component according to the present invention can be prepared by the production methods described above, and can also be prepared by separately incorporating a divalent metal compound in DOP. Specific examples of the divalent metal compound to be separately incorporated include acetates such as zinc acetate, manganese acetate, magnesium acetate, calcium acetate, barium acetate, copper acetate, iron acetate and cobalt acetate; chlorides; and hydroxides.

DOP in the organophosphorous composition comprising a predetermined amount of the divalent metal compound thus obtained according to the present invention is derived into an organophosphorous compound represented by the general formula (4):

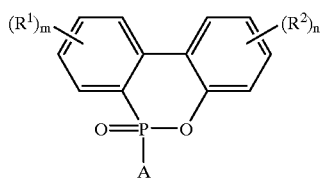

(4)

wherein $R^1$ and $R^2$ represent an organic group or a halogen atom, m and n represent an integer of 0 to 4, provided that $R^1$ and $R^2$ may be the same or different when m or n is an integer of 2 to 4, and A represents an organic group which is the same as or different from that of $R^1$ and $R^2$. The organophosphorous compound represented by the general formula (4) also contains a predetermined amount of the divalent metal compound.

The derivation of DOP into the organophosphorous compound represented by the general formula (4) can be conducted, for example, by the method of the Michael addition reaction of DOP to an α,β-unsaturated carboxylic acid compound, the method of adding to an aldehyde compound, a carbonyl compound or the like, the method of adding to an oxirane compound, the method of reacting with an aromatic compound such as phenol compound capable of reacting with DOP in the presence of a Friedel-Crafts catalyst, or the method of reacting with a compound having a hydroxyl group capable of conducting dehydration condensation with DOP.

In the general formula (4), the organic group (A) is not specifically limited and the organic group (A) is not limited to those, which are directly introduced into the derivative. In case the organic group (A) has a functional group, it includes those obtained by reacting the functional group with an organic compound on or after the introduction of the organic group (A) having a functional group into DOP.

Examples of the organic group (A) include various groups. An organophosphorous compound having an organic group containing an ester-forming functional group (B) such as hydroxyl group, carboxyl grouop, carboxylate group or the like, which is represented by the general formula (5), is used as a polyester-forming component, thereby imparting the heat resistance and flame retardancy to the polyester. Specific examples of the organophosphorous compound having an ester-forming functional group (B), which is represented by the general formula (5), include those represented by the following chemical formulas (a) to (z) and (z1) to (z4).

(a)

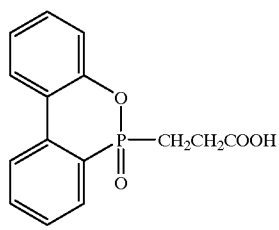

-continued (b)

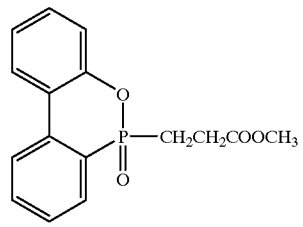

(c)

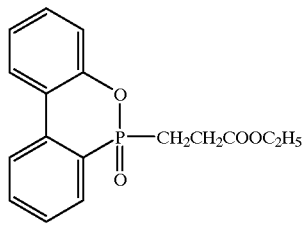

(d)

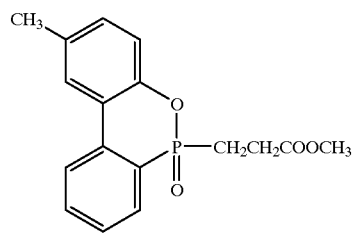

(e)

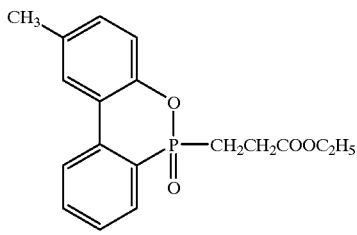

(f)

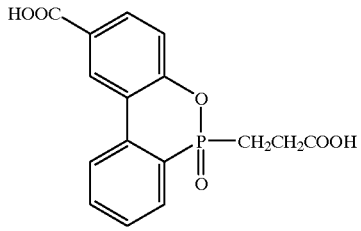

(g)

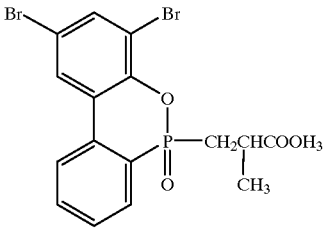

(h)
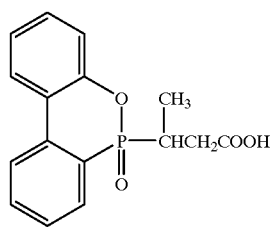
(i)
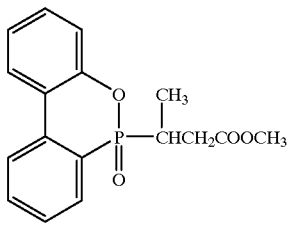
(j)
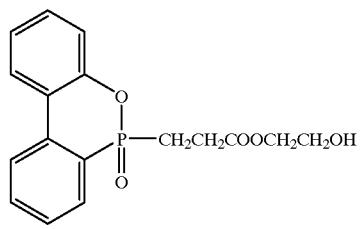
(k)
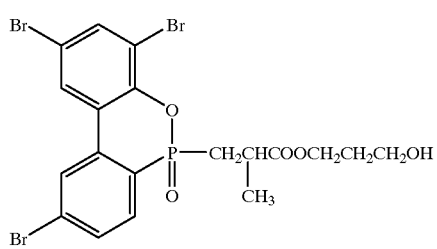
(l)
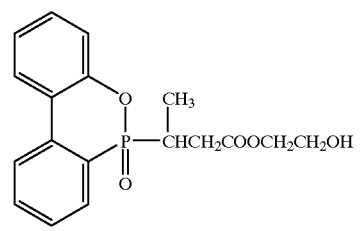
(m)
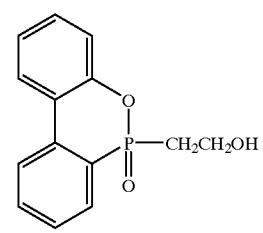
(n)
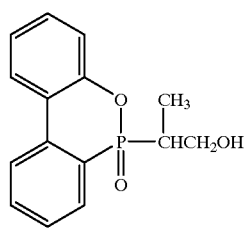
(o)
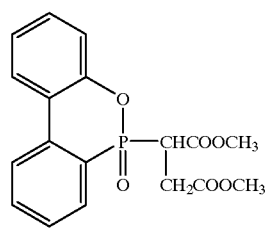
(p)
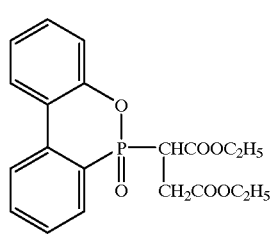
(q)
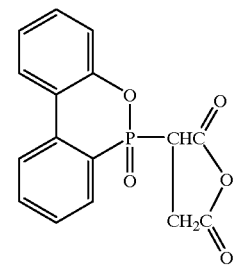
(r)
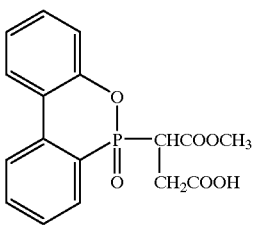
(s)
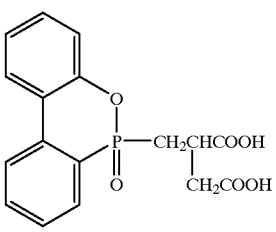

(t) 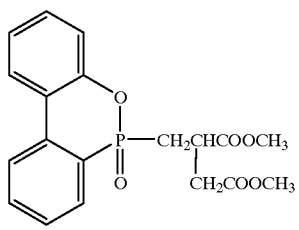

(u) 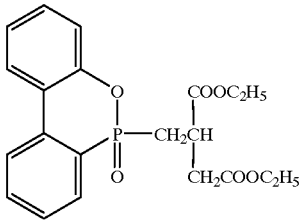

(v) 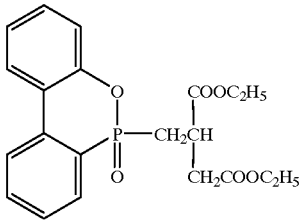

(w)

(x)

(y) 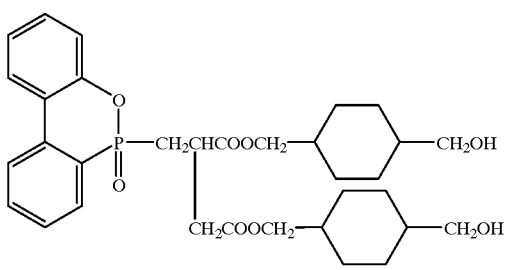

(z) 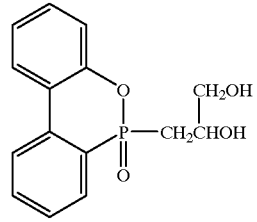

(z1) 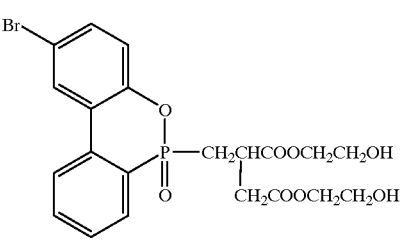

(z2) 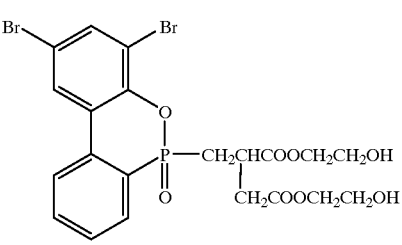

(z3) 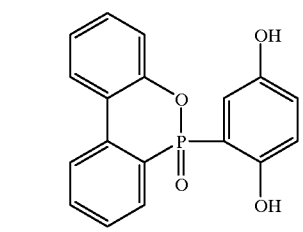

(z4) 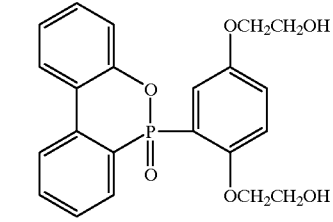

The polyester composition comprising a predetermined amount of the organophosphorous compound represented by the general formula (5) as an ester-forming component of the polyester, and a divalent metal compound in a predetermined amount based on the polyester according to the present invention can be produced in the method of producing a polyester from an ester-forming component comprising a dicarboxylic acid component and a diol component by using the organophosphorous composition comprising the organophosphorous compound represented by the general formula (5) as the ester-forming component of the polyester, and a predetermined amount of a divalent metal compound according to the present invention. The amount of organophosphorous compound represented by the general formula (5) is preferably not less than 500 ppm and not more than 50000 ppm in terms of the content of a phosphorous atom in the polyester. Such a polyester is described, for example, in Japanese Examined Patent Publication (Kokoku) No. Sho 55-41610.

Examples of the dicarboxylic acid component include aromatic dicarboxylic acids such as terephthalic acid, isophthalic acid, 2,6-naphthalenedicarboxylic acid, 1,5-naphthalenedicarboxylic acid, 4,4'-diphenyldicarboxylic acid, bis(4-carboxyphenyl)ether, bis(4-carboxyphenyl) sulfone, 1,2-bis(4-carboxyphenoxy)ethane, 5-sodium sulfoisophthalic acid, 2,5-dibromoterephtalic acid and tetrabromoterephthalic acid; aliphatic dicarboxylic acids such as adipic acid, azelaic acid and sebacic acid; and alicyclic dicarboxylic acids such as hexahydroterephthalic acid and lower alcohol ester thereof. Examples of the diol component include ethylene glycol, 1,2-propylene glycol, trimethylene glycol, tetramethylene glycol, neopentyl glycol, 1,4-cyclohexanediol, 1,4-cyclohexanedimethanol, polyethylene glycol, bisphenol A, bisphenol S and the like. As the polymerization method and polymerization catalyst, there can be used those, which have conventionally been used in the prodcution of the polyester, without any limitation. Various additives such as stabilizers and matting agents are optionally added.

In the production of the polyester, the organophosphorous composition comprising the organophosphorous compound having an organic group as an ester-forming functional group, which is represented by the general formula (5), and a predetermined amount of a divalent metal compound according to the present invention can be applied in case of employing any of the ester interchange method and direct esterification method. In case of using any method, an antimony compound as a polymerization catalyst is added in the polymerization reaction. The reduction of the antimony catalyst is suppressed by a predetermined amount of the divalent metal compound in the organophosphorous composition.

Examples of the antimony catalyst include antimony compounds such as antimony trioxide, antimony pentaoxide, antimony glycolate, antimony glycollate, antimony acetate, antimony phenolate and the like.

In the production of the polyester composition of the present invention, an organophosphorous composition containing an organophosphorous compound represented by the general formula (5) and a predetermined amount of a divalent metallic compound can be used, as described above. The polyester composition of the present invention can also be produced by adding a divalent metallic compound before or after the esterification or ester interchange, or before polymerization, in the production of a polyester using the organophosphorous compound represented by the general formula (5).

EXAMPLES

The Examples of the present invention will now be described, but the present invention is not limited to the following Examples. In the Examples, parts and percentages are by weight unless otherwise stated.

Example 1-1
(Synthesis of DOP Composition)

To 1000 parts of crude orthophenylphenol (OPP) having a purity of 95%, 4.9 parts of toluene was added. After stirring at room temperature for about one hour, a supernatant was removed. Then, 1000 parts of orthophenylphenol and 1009 parts of phosphorous trichloride were charged in a reaction vessel at a molar ratio of 1:1.25 and, after mixing at room temperature for one hour and heating the mixture to 150° C. over five hours, hydrogen chloride was evolved. To this was added 5.9 parts of zinc chloride, and then the reaction was conducted at 200° C. for four hours to obtain 6-chloro-(6H)-dibenzo-(c,e)(1,2)-oxaphosphorine (DOP-X).

The resulting DOP-X was purified by adding 500 parts of toluene to DOP-X, stirring at room temperature for about one hour and removing a supernatant.

To this was added 77 parts of water so that a molar ratio of orthophenylphenol to water is 1:1. Then, 1000 parts of toluene was added and the hydrolysis was conducted under reflux and, at the same time, a hydrogen chloride gas evolved was removed.

After 1000 Parts of hot water at 50–60° C. was added and stirring, the aqueous layer was removed by separation and the resultant was washed with 500 parts of water three times. Water in the oil layer was removed by azetropic dehydration and the oil layer was treated with activated carbon, followed by the addition of 2000 parts of water, dissolution and cooling. The solid was collected and washed with 1000 parts of water. The solid was dehydrated at 130° C. under reduced pressure of 13.3 kPa to obtain powdered 6-oxo-(6H)-dibenzo-(c,e)(1,2)-oxaphosphorine (DOP). DOP could also be recovered from the filtrate.

The content of metallic zinc and that of a chlorine atom in the DOP composition were measured by atomic absorption spectrometry and ion chromatography. The content of the organic compound as impurity was determined by NMR analysis and IR analysis. There are shown in Table 1.

Example 2-1

The same operation as in Example 1-1 was conducted up to the hydrolysis reaction, except that DOP-X was not treated with toluene after its production. The product was cooled to separate a white granular product. Then, 8000 Parts of an aqueous 8% sodium hydroxide solution was added and this solution was neutralized. The solution was filtered through activated carbon and an aqueous 20% sulfuric acid solution was gradually added to the filtrate to obtain a white crystal. The white crystal was dehydrated at 130° C. under reduced pressure of 13.3 kPa to obtain a powdered DOP composition. The content of metallic zinc, that of a chlorine atom and that of an organic compound as impurity in the DOP composition are shown in Table 1.

Example 3-1

In the same manner as in Example 1-1, except that DOP-X was not treated with toluene after its production, a powdered DOP composition was obtained. The content of metallic zinc, that of a chlorine atom and that of an organic compound as impurity in the DOP composition are shown in Table 1.

Example 4-1

The same operation as in Example 1-1 was conducted up to the hydrolysis reaction, except that DOP-X was not treated with toluene after its production, and a powdered DOP composition was obtained in the same manner as in Example 1-1, except that the times of washing with water was changed to two. The content of metallic zinc, that of a chlorine atom and that of an organic compound as impurity in the DOP composition are shown in Table 1.

Example 5-1

The same hydrolysis reaction as in Example 1-1 was conducted, except that OPP was not treated with toluene and DOP-X was not treated with toluene after its production, and a powdered DOP composition was obtained in the same manner as in Example 1-1. The product was cooled to separate a white granular product. Then, 8000 Parts of an aqueous 8% sodium hydroxide solution was added and this solution was neutralized. The solution was filtered through activated carbon and an aqueous 20% sulfuric acid solution was gradually added to the filtrate to obtain a white crystal. The white crystal was dehydrated at 130° C. under reduced pressure of 13.3 kPa to obtain a powdered DOP composition. The content of metallic zinc, that of a chlorine atom and that of an organic compound as impurity in the DOP composition are shown in Table 1.

Example 6-1

The same hydrolysis reaction as in Example 1-1 was conducted, except that OPP was not treated with toluene. The product was cooled to separate a white granular product. Then, 8000 Parts of an aqueous 8% sodium hydroxide solution was added and this solution was neutralized. The solution was filtered through activated carbon and an aqueous 20% sulfuric acid solution was gradually added to the filtrate to obtain a white crystal. The white crystal was dehydrated at 130° C. under reduced pressure of 13.3 kPa to obtain a powdered DOP composition. The content of metallic zinc, that of a chlorine atom and that of an organic compound as impurity in the DOP composition are shown in Table 1.

Comparative Example 1-1

The same hydrolysis reaction as in Example 1-1 was conducted, except that DOP-X was not treated with toluene after its production. Then, the product was cooled by adding 1000 parts of toluene. The product was cooled and the solid product was collected by filtration. The solid product was washed with 300 parts of toluene to obtain a powdered DOP composition. The content of metallic zinc, that of a chlorine atom and that of an organic compound as impurity in the DOP composition are shown in Table 1.

Comparative Example 2-1

The same operation as in Example 1-1 was conducted up to the production of DOP-X. Then, 8000 parts of water was added and the hydrolysis was conducted under reflux in the presence of excess water. The product was cooled and a white granular product was filtered. Then, 8000 Parts of an aqueous 8% sodium hydroxide solution was added and this solution was neutralized. The solution was filtered through activated carbon and an aqueous 20% sulfuric acid solution was gradually added to the filtrate to obtain a white crystal. The white crystal was dehydrated at 130° C. under reduced pressure of 13.3 kPa to obtain a powdered DOP composition. The content of metallic zinc, that of a chlorine atom and that of an organic compound as impurity in the DOP composition are shown in Table 1.

Example 1-2
(Synthesis of DOP Derivative Composition)

Under a nitrogen atmosphere at 160° C.,216 Parts of DOP obtained in Example 1-1, 130 parts of itaconic acid and 346 parts of ethylene glycol were subjected to react for two hours while distilling off water to obtain a compound corresponding to the compound (x). An insoluble matter complex was not found in the resulting compound.

Examples 2-2 to 6-2

In the same manner as in Example 1-2, except that DOP obtained in Examples 2-1 to 6-1 was used in place of DOP obtained in Example 1-1, compounds corresponding to the compound (x) were produced. An insoluble matter complex was not found in the resulting compounds.

Comparative Example 1-2

In the same manner as in Example 1-2, except that DOP obtained in Comparative Example 1-1 was used in place of DOP obtained in Example 1-1, a compound corresponding to the compound (x) was produced. An insoluble matter complex was found in the resulting compound.

Comparative Example 2-2

In the same manner as in Example 1-2, except that DOP obtained in Comparative Example 2-1 was used in place of DOP obtained in Example 1-1, a compound corresponding to the compound (x) was produced. An insoluble matter complex was not found in the resulting compound. DOP obtained in Comparative Example 2-1 was used after grinding because it is flaky.

Example 1-3
(Synthesis of Polyester)

In an autoclave made of stainless steel equipped with a stirrer, a distillation column and a pressure controller, 401 parts of terephthalic acid, 67 parts (content of phosphorous based on the resulting polyester: 6000 ppm) of the DOP derivative composition obtained in Example 1-2 and 259 parts of ethylene glycol were charged. Then, 16 parts of an ethylene glycol solution of antimony trioxide (14 g/liter) and triethylamine were added and the mixture was subjected to esterify at 230° C. under a gauge pressure of 0.245 MPa for two hours while removing water to be produced. Subsequently, the pressure in the system was gradually decreased to 13.3 Pa while rising the temperature in the system to 275° C. for one hour, and then the copolymerization reaction was conducted under these conditions for two hours. The intrinsic viscosity of the resulting polyester was 0.620, while the value L and value b of as the color value were respectively 56.4 and 3.5.

Intrinsic viscosity: It was measured at 30° C. using a mixed solution of phenol and 1,1,2,2-tetrachloroethane in a weight ratio of 3:2.

Color value: It was measured by a Hunter color difference meter using a polyester chip. The larger the value L, the stronger the whiteness. The larger the value b, the stronger the yellowish color.

Examples 2-3 to 6-3

In the same manner as in Example 1-3, except that the DOP derivative composition obtained in Examples 2-2 to 6-2 was used in place of the DOP derivative composition obtained in Example 1-2, polyesters were produced. The intrinsic viscosity, value L and value b of the resulting polyesters are shown in Table 1.

Comparative Examples 1-3 to 2-3

In the same manner as in Example 1-3, except that the DOP derivative composition obtained in Comparative Examples 1-2 to 2-2 was used in place of the DOP derivative composition obtained in Example 1-2, polyesters were produced. The intrinsic viscosity, value L and value b of the resulting polyesters are shown in Table 1.

Example 7

In the same manner as in Example 1-3, except that the DOP derivative composition obtained in Comparative Example 2-2 was used in place of the DOP derivative composition obtained in Example 1-2 and 0.84 parts (10 ppm/polyester) of an ethylene glycol solution of zinc acetate (20 g/liter) was added before the esterification, a polyester was produced. The intrinsic viscosity, value L and value b of the resulting polyester are shown in Table 1.

The results of the Examples, Comparative Examples, Application Examples and Comparative Application Examples described above are summarized in Table 1.

TABLE 1

|  | Examples 1-1 | Examples 2-1 | Examples 3-1 | Examples 4-1 | Examples 5-1 | Examples 6-1 | Comparative Examples 1-1 | Comparative Examples 2-1 |
|---|---|---|---|---|---|---|---|---|
| DOP composition |  |  |  |  |  |  |  |  |
| Content of metallic zinc (ppm) | 85 | 32 | 98 | 250 | 30 | 33 | 2400 | 1 |
| Content of chlorine atom (ppm) | 110 | 94 | 125 | 211 | 105 | 102 | 2350 | 220 |
| Content of impurity (%) | 0 | 0.5 | 0 | 0 | 6 | 1 | 5 | 5 |
| Form | Powder | Powder | Powder | Powder | Bulk | Powder | Powder | Bulk |

|  | Examples 1-2 | Examples 2-2 | Examples 3-2 | Examples 4-2 | Examples 5-2 | Examples 6-2 | Comparative Examples 1-2 | Comparative Examples 2-2 |
|---|---|---|---|---|---|---|---|---|
| Insoluble matter complex | Not found | Not found | Not found | Not found | Not found | Not found | Found | Not found |

|  | Examples 1-3 | Examples 2-3 | Examples 3-3 | Examples 4-3 | Examples 5-3 | Examples 6-3 | Comparative Examples 1-3 | Comparative Examples 2-3 | Examples 7 |
|---|---|---|---|---|---|---|---|---|---|
| Amount of zinc to be added (ppm) | — | — | — | — | — | — | — | — | 10 |
| Polyester composition |  |  |  |  |  |  |  |  |  |
| Amount of metallic zinc (ppm) | 11 | 4 | 13 | 33 | 4 | 4 | 320 | 0 | 10 |
| Intrinsic viscosity | 0.626 | 0.610 | 0.605 | 0.613 | 0.621 | 0.615 | 0.615 | 0.620 | 0.625 |
| Color value |  |  |  |  |  |  |  |  |  |
| Value L | 56.4 | 56.0 | 56.3 | 57.1 | 55.8 | 56.1 | 55.9 | 51.0 | 56.5 |
| Value b | 3.5 | 4.2 | 3.5 | 4.0 | 7.8 | 5.0 | 8.1 | 7.3 | 7.7 |

As is apparent from the results of Table 1, a color tone of a polyester is maintained at a white color even in case of using an antimony catalyst by controlling the content of a divalent metal within a predetermined range. A complex is not formed because of low content of the divalent metal and, moreover, the formation of diethylene glycol as a by-product can be suppressed by reducing the content of a chlorine (halogen) atom. Furthermore, powdered DOP can be obtained by reducing an organic impurity.

What is claimed is:

1. An organophosphorous composition comprising, as a principal component, an organophosphorous compound represented by the general formula (1):

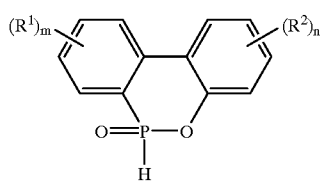

(1)

wherein $R^1$ and $R^2$ represent an organic group or a halogen atom, and m and n represent an integer of 0 to 4, provided that $R^1$ and $R^2$ may be the same or different when m or n is an integer of 2 to 4, the composition further comprising, as a compound other than the organophosphorous compound, a divalent metallic compound in an amount more than 30 ppm and not more than 2300 ppm in terms of a divalent metal based on the organophosphorous compound.

2. The organophosphorous composition according to claim 1, wherein the divalent metal is zinc.

3. The organophosphorous composition according to claim 1, wherein the compound other than the organophosphorous compound is a halogen compound, the content of the halogen compound is not more than 250 ppm in terms of an amount of a halogen atom based on the organophosphorous compound.

4. The organophosphorous composition according to claim 1, which does not substantially contain an organic compound other than the organophosphorous compound.

5. The organophosphorous composition according to claim 1, which is in the form of powder.

6. A method of producing an organophosphorous compound represented by the general formula (1):

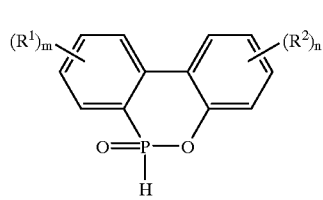

(1)

wherein $R^1$ and $R^2$ represent an organic group or a halogen atom, and m and n represent an integer of 0 to 4, provided that $R^1$ and $R^2$ may be the same or different when m or n is an integer of 2 to 4, which comprises the steps of:

reacting an orthophenylphenol compound represented by the general formula (2):

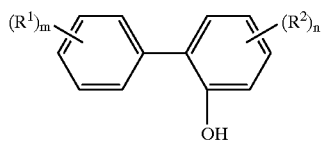

(2)

wherein $R^1$ and $R^2$ are as defined above, with phosphorous trihalide ($PX_3$: X represents a halogen atom) and condensing the reaction product with heating in the presence of a Friedel-Crafts catalyst containing zinc chloride to produce an organophosphorous compound represented by the general formula (3):

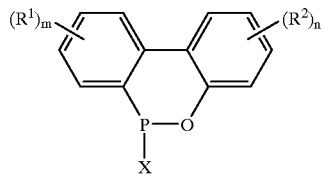

(3)

wherein $R^1$ and $R^2$ are as defined above and X represents a halogen atom; and hydrolyzing the compound represented by the general formula (3) with water; the compound represented by the general formula (3) and water in the hydrolysis step are used in an equimolar ratio and that the method further comprises a step of purifying the organophosphorous compound represented by the general formula (1) by further hydrolyzing the organophosphorous compound represented by the general formula (1), which is obtained by passing through the hydrolysis step, followed by cyclodehydration.

7. The method of producing the organophosphorous compound according to claim 6, wherein the compound represented by the general formula (2), which has purity of not less than 80% and less than 100%, is subjected to the reaction after remarkably purifying by washing with an organic solvent.

8. The method of producing the organophosphorous compound according to claim 6, wherein the compound represented by the general formula (3) is subjected to a hydrolysis step after subjected to a purification step.

9. The method of producing the organophosphorous compound according to claim 6, wherein the content of a zinc compound is adjusted more than 30 ppm and not more than 2300 ppm in terms of metallic zinc based on the organophosphorous compound represented by the general formula (1).

10. The method of producing the organophosphorous compound according to claim 6, wherein the content of a halogen compound is not more than 250 ppm in terms of an amount of a halogen atom based on the organophosphorous compound represented by the general formula (1).

11. The method of producing the organophosphorous compound according to claim 6, wherein an organic compound other than the organophosphorous compound represented by the general formula (1) is not substantially contained.

12. The method of producing the organophosphorous compound according to claim 6, wherein the organophosphorous compound represented by the general formula (1) is in the form of powder.

13. An organophosphorous composition produced by derivation of an organophosphorous compound in the organophosphorous composition of claim 1 into an organophosphorous compound represented by the general formula (4):

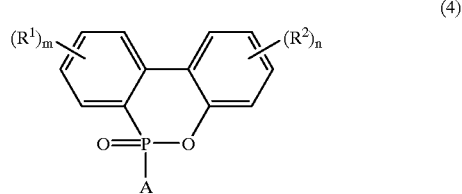

(4)

wherein $R^1$ and $R^2$ represent an organic group or a halogen atom, m and n represent an integer of 0 to 4, provided that $R^1$ and $R^2$ may be the same or different when m or n is an integer of 2 to 4, and A represents an organic group which is the same as or different from that of $R^1$ and $R^2$.

14. The organophosphorous composition according to claim 13, wherein the organic group (A) in the general formula (4) is an organic group containing an ester-forming functional group (B).

15. A polyester composition comprising, as a principal component, a polyester obtained from an ester-forming component containing a dicarboxylic acid component and a diol component, the polyester containing, as the ester-forming component, an organophosphorous compound represented by the general formula (5):

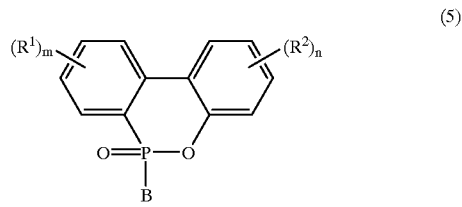

(5)

wherein $R^1$ and $R^2$ represent an organic group or a halogen atom, m and n represent an integer of 0 to 4, provided that $R^1$ and $R^2$ may be the same or different when m or n is an integer of 2 to 4, and B represents an ester-forming functional group, the polyester composition containing a divalent metallic compound in an amount not less than 1 ppm and not more than 150 ppm in terms of a divalent metal based on the polyester.

16. The polyester composition according to claim 15, which contains a divalent metallic compound in an amount not less than 1 ppm and not more than 50 ppm in terms of a divalent metal based on the polyester.

17. The polyester composition according to claim 15, wherein the divalent metal is zinc.

18. The polyester composition according to claim 15, which contains an organophosphorous compound represented by the general formula (5) as the ester-forming component of the polyester in an amount not less than 500 ppm and not more than 5000 ppm in terms of an amount of a phosphorous atom.

19. A method of producing the polyester composition of claim 15, which comprises reacting an ester-forming component containing a dicarboxylic acid component and a diol component, wherein the organophosphorous composition of claim 14 is used as the dicarboxylic acid component and/or the diol component.

20. The method of producing the polyester composition of claim 19, wherein an antimony compound is used as a condensation catalyst of the polyester.

* * * * *